(12) United States Patent
Minteer et al.

(10) Patent No.: US 9,285,331 B2
(45) Date of Patent: Mar. 15, 2016

(54) SYSTEMS AND METHODS FOR DETECTING MATERIALS IN FOOD PRODUCTS

(71) Applicant: Binergy Scientific, Inc., Salt Lake City, UT (US)

(72) Inventors: Shelley Minteer, Salt Lake City, UT (US); Vojtech Svoboda, Atlanta, GA (US)

(73) Assignee: BINERGY SCIENTIFIC, INC., Salt Lake City, UT (US)

( * ) Notice: Subject to any disclaimer, the term of this patent is extended or adjusted under 35 U.S.C. 154(b) by 0 days.

(21) Appl. No.: 14/068,417

(22) Filed: Oct. 31, 2013

(65) Prior Publication Data

US 2014/0116158 A1    May 1, 2014

Related U.S. Application Data

(60) Provisional application No. 61/720,820, filed on Oct. 31, 2012.

(51) Int. Cl.
*G01N 33/02* (2006.01)
*G01N 27/02* (2006.01)
*B01L 3/00* (2006.01)

(52) U.S. Cl.
CPC ............... *G01N 27/02* (2013.01); *B01L 3/502* (2013.01); *G01N 33/02* (2013.01); *B01L 2200/0668* (2013.01); *B01L 2300/0645* (2013.01)

(58) Field of Classification Search
None
See application file for complete search history.

(56) References Cited

U.S. PATENT DOCUMENTS 7,771,658 B2 *   8/2010   Larsen .................... 422/82.01

* cited by examiner

*Primary Examiner* — Robert R Raevis
(74) *Attorney, Agent, or Firm* — Harness, Dickey & Pierce, P.L.C.

(57) ABSTRACT

A device, method and system for measuring analytes in a solution or suspension. The device includes a housing, a sample chamber, one or more pumps, one or more detectors, one or more stirrers, electrical contacts, a magnetic manipulator and a lid. A sample cartridge for a device that measures analytes, the cartridge comprising a first outer compartment, a second outer compartment, and a middle compartment, wherein the first outer compartment and the second outer compartment are interconnected to the middle compartment by channels.

10 Claims, 3 Drawing Sheets

SYSTEMS AND METHODS FOR DETECTING MATERIALS IN FOOD PRODUCTS

CROSS-REFERENCE TO RELATED APPLICATIONS

Figure 1A:
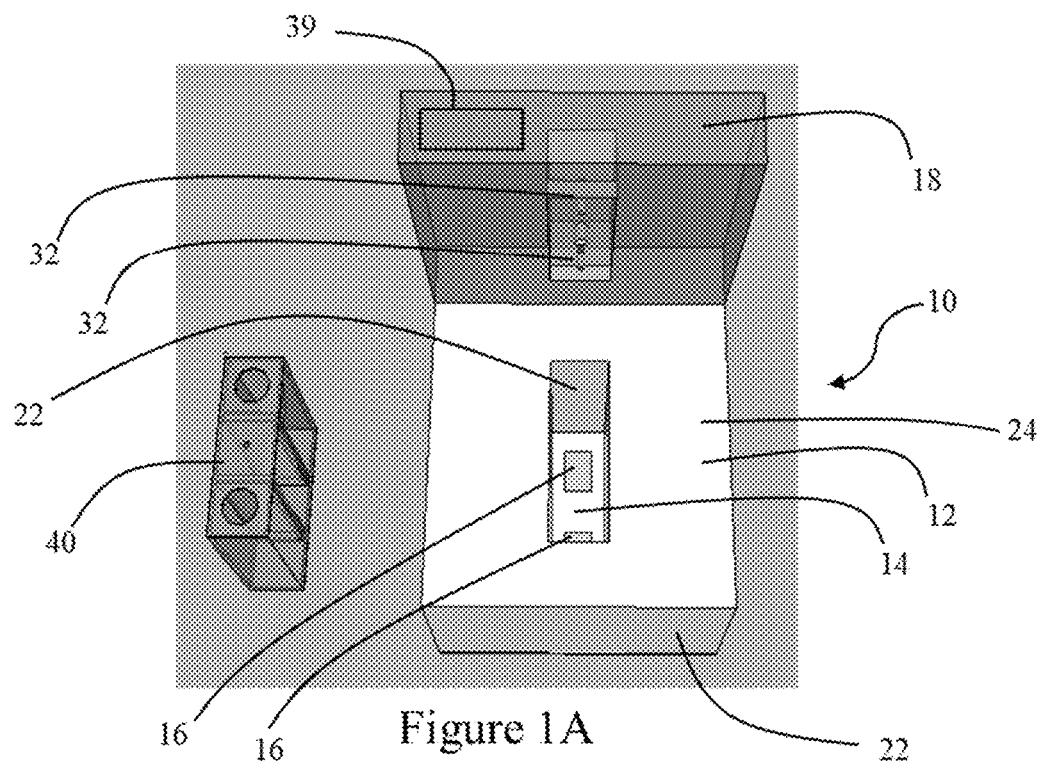

This application claims the benefit of U.S. Provisional Application No. 61/720,820, filed on Oct. 31, 2012. The entire disclosure of the above application is incorporated herein by reference.

INTRODUCTION

The present technology relates to systems, devices and methods for the detection of materials in foods and other products intended for human or animal consumption or contact, including allergens, bacteria, viruses, herbicides, pesticides and other contaminants.

Public awareness of the use of pesticides, insecticides, herbicides, and other synthetic chemicals in farming is increasing. For example, organophosphates, which are common active ingredients in insecticides and herbicides, have been associated with impaired memory and concentration, disorientation, depression, irritability, headaches, insomnia, onset of attention deficit hyperactivity disorder (ADHD), Alzheimer's disease, chronic fatigue, and cancer. Awareness of the toxic effects of pesticides has encouraged many consumers to look for healthy alternatives, such as foods that are produced by organic farming.

Organic farming relies on natural methods for crop cultivation, such as the use of crop management techniques that do not employ non-natural herbicides, fertilizers and pesticides. For example, organic farms refrain from using synthetic pesticides, hormones, additives, and genetically modified organisms (GMOs). In the United States, the Organic Foods Production Act (OFPA) governs the production of, and the identification of, organic foods. Although the labeling of foods as organic is regulated, foods that are improperly labeled as "organic" have been found in grocery stores. In general, organic food might be easily mixed and contaminated with non-organic food during transportation, storage, and sale.

Additionally, consumers are also continually becoming more aware of materials in foods and other consumer products which may create adverse allergic, metabolic and other physiologic reactions. For example, ingestion of an allergen can lead to serious consequences, including death. Peanuts, gluten and lactose are examples of foods materials that are commonly avoided by those with allergies or other material sensitivities.

While laws and regulations exist that require the labeling of ingredients in foods, cosmetics and other compositions for human contact or consumption, consumers cannot necessarily be assured that such products do not contain materials that may create adverse health effects. For example, some products are not subject to labeling requirements (such as produce), and some materials (such as herbicides and pesticides) may be present in trace amounts. Moreover, some products may be mislabeled, or subject to tampering, adulteration or accidental contamination.

While analytical methods exist for identifying contaminants, such methods are typically expensive and otherwise not convenient at the retail or consumer stages of product production, delivery and use. Most commonly, these methods are instrumental methods that require expensive laboratory instrumentation, such as high performance liquid chromatography (HPLC), gas chromatography-mass spectrometry (GC-MS), etc. Thus, there is a keen need for convenient and inexpensive means for retailers and consumers to analyze foods and other materials intended for human or animal consumption for undesired materials. For example, there is a need to test foods to determine whether they are truly "organic," or to determine whether they contain an allergen.

SUMMARY

The present technology provides systems, devices and methods for detecting undesired materials in consumer products. In various embodiments, such systems comprise a point-of-use analytical device and disposable test element suitable for detecting or measuring one or more analytes in a product sample.

For example, a device may comprise a housing, a sample chamber, one or more pumps, one or more detectors, a stirrer, electrical contacts, a magnetic manipulator and a closable lid. The housing comprises a floor and walls that define an interior compartment.

The sample chamber is located within the housing. The sample chamber is configured to accept the insertion of a sample cartridge comprising three chambers and electrodes. The electrical contacts are located within the sample chamber for electronic and/or fluidic connection to the sample cartridge in such a manner that the electrical contacts can receive a detectable signal from the sample cartridge. The stirrer is functional to stir or mix contents of the sample cartridge pneumatically, magnetically, acoustically or by sonication, when the sample cartridge is inserted into the sample chamber.

The magnetic manipulator can be located adjacent to the sample chamber and coupled to a mobile platform. In some embodiments, magnetic nanoparticles can be present within the sample cartridge. When a sample cartridge containing magnetic nanoparticles is inserted into the sample chamber of the device, the magnetic manipulator can induce a magnetic field that attracts the magnetic nanoparticles and drags them to a desired location within the sample cartridge by means of the mobile platform. Therefore, the nanoparticles can act as carriers for an analyte to be detected.

The one or more detectors are located within the housing. A sample can be transferred into a sample cartridge, and the sample cartridge can be placed into the sample chamber of the device. The one or more detectors can detect the presence of analytes within the samples. The one or more detectors can measure pH, conductivity, current, potential, capacitance, resistance, charge, photons, temperature, viscosity, and combinations thereof. The one or more detectors can be a potentiostat, galvanostat, multimeter, electrochemical impedance analyzer, ultraviolet-visible (UV-Vis) spectrometer, near infrared spectrometer, Fourier transform infrared spectrometer, photomultiplier tube, photodiode, charge-coupled device (CCD), and combinations thereof. In some embodiments, the photomultiplier tube and/or photodiode are connected to a mobile platform, whereby the mobile platform allows for controlled movement of the photomultiplier tube and/or photodiode along the sample cartridge for measurement through various locations of a sample cartridge. The device can also comprise at least one signal processing component, a data storage component, software equipment, data transfer and communication modules, a bar code reader, and/or a user interface.

The lid is functionally coupled to the housing by a hinge, which enables an open conformation and a closed conformation. In the closed conformation, light exterior to the device is unable to enter the interior compartment of the device. Additionally, the lid comprises seals, actuators and injectors. The actuators are functional to position the seals above a sample cartridge to produce a hermetic seal on top of the sample cartridge. The injectors are hermetically integrated through the seals. In various embodiments, the injectors can inject gas, such as air, or a fluid into the sample cartridge.

The present technology also provides a sample cartridge for a device that measures analytes in a sample. The cartridge comprises two outer solution compartments separated by a middle compartment, wherein the two outer solution compartments are capable of accepting solutions, and transfer of the solutions from the outer solution compartments to the middle compartment does not occur without an increase or decrease in pressure induced by injectors. The process of solution transfer from both outer compartments can be independent of each other. A filter can be integrated into at least one of the two outer solution compartments. The two outer solution compartments and the middle compartment comprise a front face and a back face, wherein both faces are composed of an optically clear plastic through which a detectable signal can pass. The cartridge can comprise electrodes that interact with electrical contacts within a sample chamber of a device for detecting analytes when the cartridge is inserted into such a device. The sample cartridge can be packaged within a plastic or aluminum seal to ensure a sterile internal environment before testing, and to prolong the lifetime of the cartridge.

Further, the present technology provides a system for detecting unwanted materials in a consumer product. The system comprises a product sample cartridge comprising a product sample reservoir and a detection port in communication with the product sample reservoir; and a detection apparatus comprising a receptacle for the cartridge, a detection device operable to communicate with the detection port of the sample cartridge, and a user interface operable to display results of the analysis of the consumer product. The system can additionally comprise an analytical element operable to detect the unwanted material and produce a signal regarding the presence of the unwanted material. The analytical element can be contained within the product sample cartridge, the detection device, or a combination thereof. The signal can be mechanical, thermal, electrical or optical.

Additionally, the present technology provides methods for measuring analytes in a sample. The sample can be a consumer product or the sample can be an element of a chemical or biochemical assay. The method comprises obtaining a sample cartridge comprising a first outer compartment, a second outer compartment, a middle compartment, and integrated electrodes and/or screen printed electrodes, wherein the first outer compartment and the second outer compartment are interconnected to the middle compartment by channels; obtaining a measuring device comprising a sample chamber, one or more pumps, one or more detectors, one or more stirrers, electrical contacts, a magnetic manipulator and a closable lid, wherein the closable lid comprises seals, actuators and injectors; transferring a solvent into the first (solvent) outer compartment of the sample cartridge; preparing a sample in a sample solvent; transferring the sample into the second (sample) outer compartment of the sample cartridge; inserting the sample cartridge into the sample chamber of the measuring device; and closing the lid. In some embodiments, a filter is integrated into at least one of the outer compartments of the sample cartridge allowing for filtering of the solvent or sample when being transferred into the sample cartridge from large solid particles and or agglomerates, which could impair the detection or clog the channels. When the lid is closed, the actuators position the seals to produce a hermetic seal on the outer compartments of the sample cartridge. Alternatively, the seals can be mechanically positioned on the sample cartridge to provide a hermetic seal, induced by manually closing the closable lid. The injectors can then be operated to induce pneumatic pressure into the outside chambers, thereby transferring the sample and the solvent from the outer compartments, through the channels, and into the middle compartment. The transfer of sample and solvent solutions can be independent of each other and can proceed in any order or simultaneously. Alternatively, pressure might be induced to the middle chamber and provide a solution transfer by controlling and releasing pressure to the outer compartments. This method allows for contactless and cross-contamination free transferring of sample and solvent from within the sample cartridge. In some embodiments, the contents of the middle compartments are stirred or mixed pneumatically, magnetically, acoustically, or by sonication.

In some embodiments, magnetic particles or magnetic nanoparticles can be transferred into the sample in the first outer compartment of the sample cartridge. Optionally, magnetic particles or magnetic nanoparticles can be inserted into and enclosed in the sample outer chamber during fabrication of the sample cartridge. The magnetic particles/nanoparticles can be modified with a detection active material, which may bind an analyte. The magnetic particles/nanoparticles can then be transferred into the middle compartment by a magnetic manipulator for contactless, and cross-contamination free transfer. When the detection active material is bound to an analyte, the analyte is carried and dragged into the middle compartment of the sample cartridge along with the magnetic particles/nanoparticles. The magnetic manipulator can be coupled to a mobile platform. The magnetic manipulator can induce a magnetic field capable of dragging the magnetic particles/nanoparticles from the first outer compartment of the sample cartridge to the middle compartment.

According to the method, detecting is performed by a potentiostat, galvanostat, multimeter, electrochemical impedance analyzer, UV-Vis spectrometer, near infrared spectrometer, Fourier transform infrared spectrometer, photomultiplier tube, photodiode, CCD, thermocouple, or combinations thereof. The one or more detectors measure pH, conductivity, current, potential, capacitance, resistance, charge, photons, temperature, viscosity, or combinations thereof.

In various embodiments, the present technology provides food safety and quality control at the consumer/end user stage. The present technology also allows generation and use of a database of food products parameters sets and their application as a comparative analytical tool to evaluate food freshness and quality. Further areas of applicability will become apparent from the description provided herein.

DRAWINGS

The present technology will become more fully understood from the detailed description and the accompanying drawings. Corresponding reference numerals indicate corresponding parts throughout the several views of the drawings.

Figure 1B:
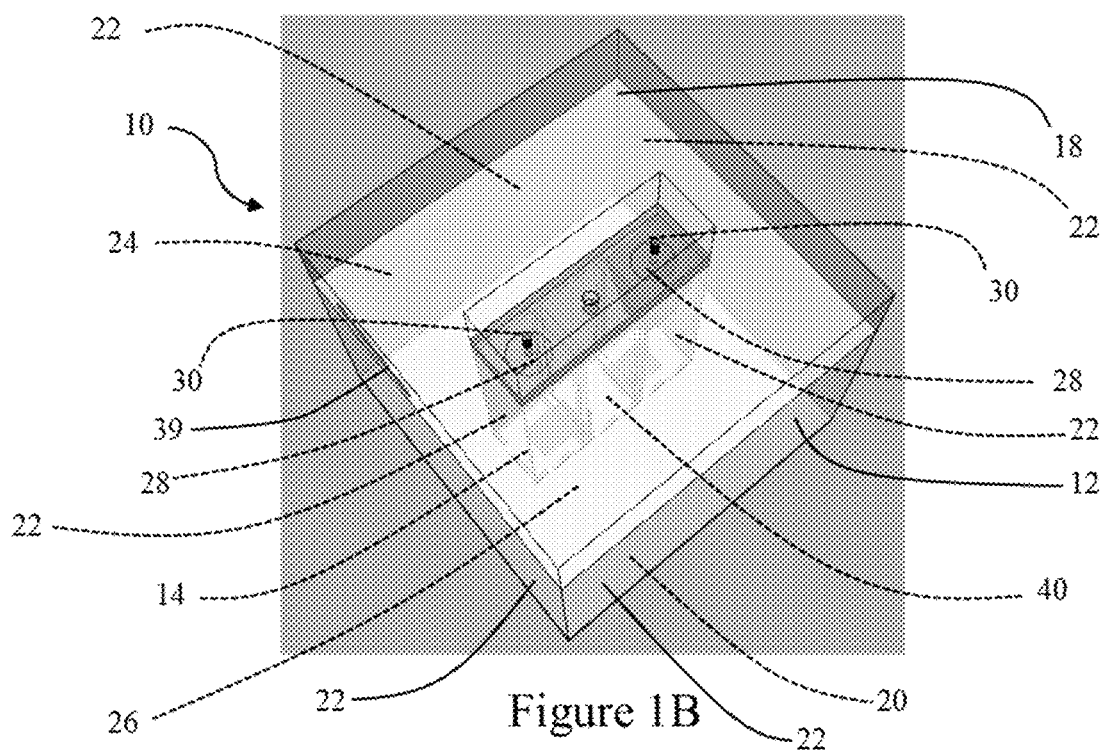
Figure 2A:
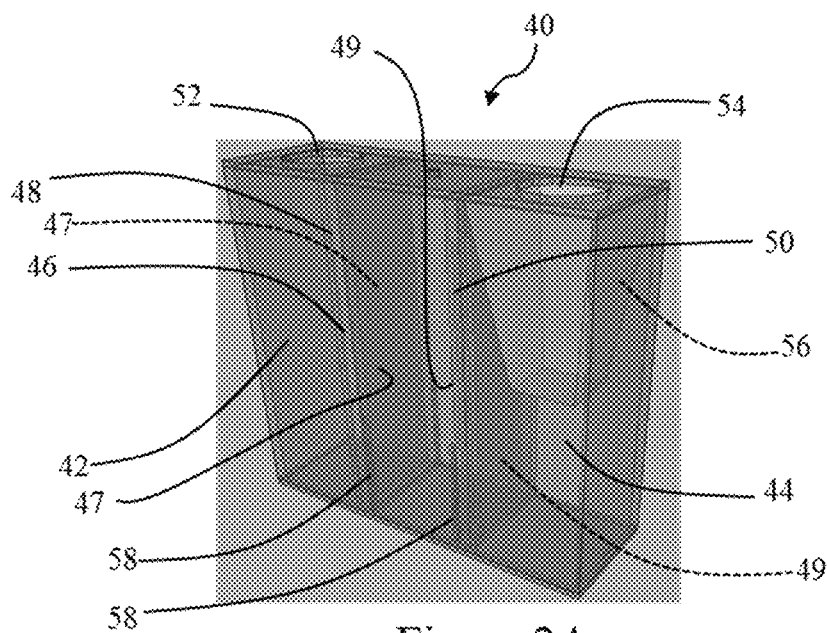
Figure 2B:
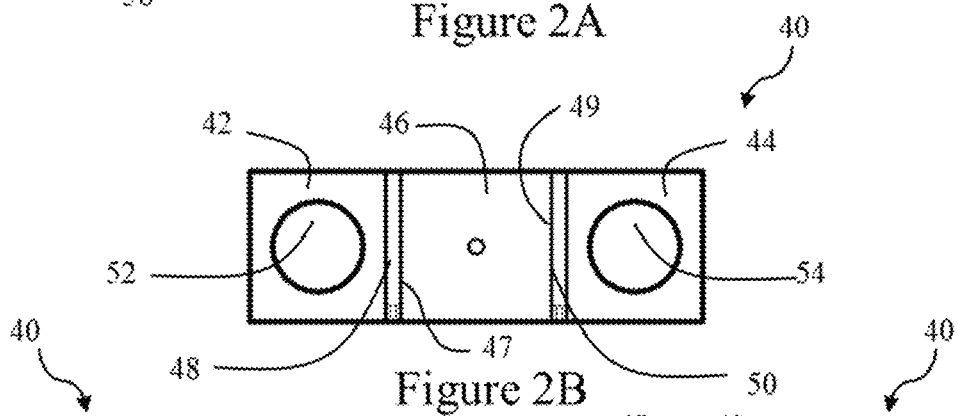
Figures 2C, 2D:
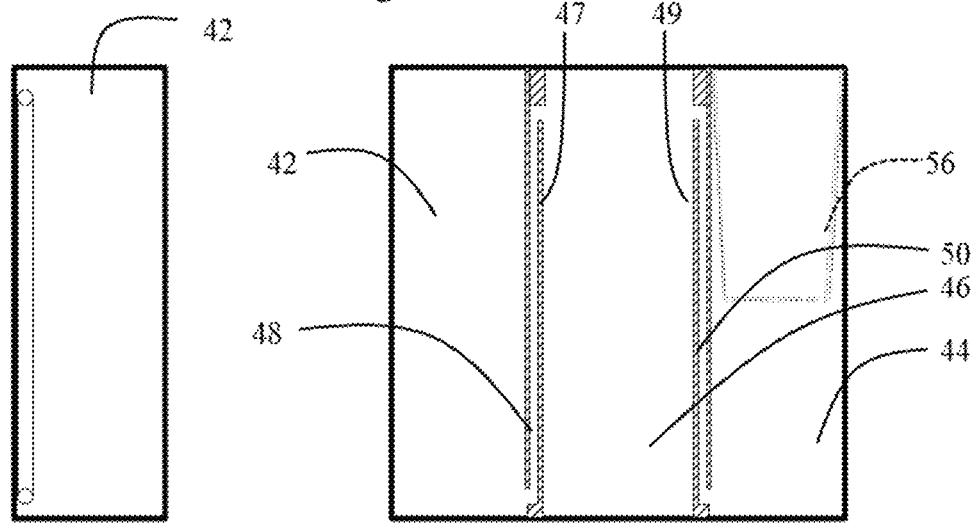
Figure 3:
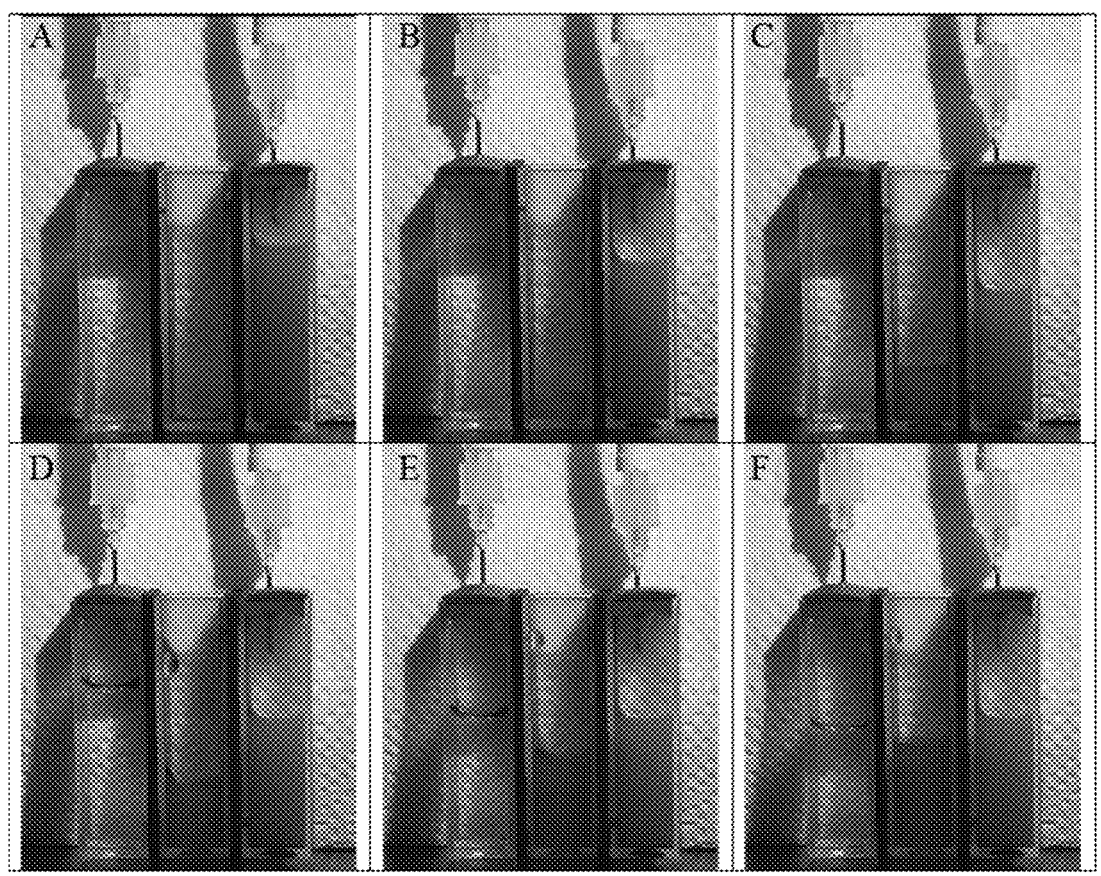

FIGS. 1A and 1B are a graphic illustration depicting a device for measuring analytes in a sample in an opened configuration (FIG. 1A), and in a closed configuration (FIG. 1B);

FIGS. 2A-2D are a graphic illustration depicting a sample cartridge for a device that measures analytes in a 3-dimensional orientation (FIG. 2A), from above (FIG. 2B), from a side face (FIG. 2C), and from a front face (FIG. 2D); and FIG. 3 is a series of six photographs (A-F) showing the pneumatic filling of a middle compartment of a sample cartridge over time from the first outer (solvent) compartment and the second outer (sample) compartment.

It should be noted that the figures set forth herein are intended to exemplify the general characteristics of devices and methods among those of the present technology, for the purpose of the description of certain embodiments. These figures may not precisely reflect the characteristics of any given embodiment, and are not necessarily intended to define or limit specific embodiments within the scope of this technology.

DETAILED DESCRIPTION

The following description of technology is merely exemplary in nature of the composition, manufacture and use of one or more inventions, and is not intended to limit the scope, application, or uses of any specific invention claimed in this application or in such other applications as may be filed claiming priority to this application, or patents issuing therefrom. A non-limiting discussion of terms and phrases intended to aid understanding of the present technology is provided at the end of this Detailed Description.

The present technology provides systems, devices and methods for detecting undesired materials in consumer products. Such "consumer products" include any product intended for consumption, contact, or other use by a human or animal (such as a household pet or other companion animal). Consumer products include, for example, foods (such as produce, meats, dairy, food components, and processed foods), cosmetics, personal care compositions (such as shampoos and skin care products), and health care products (such as over-the-counter drugs, herbal products, and nutritional supplements). As referred to herein, such "undesired materials" include chemicals, chemical compositions, organisms or organism by-products that are aesthetically, physiologically, or otherwise undesired by a consumer of the consumer product. For example, the technology provides methods for detecting food-born pathogen bacteria and viruses in the analyzed sample. Such pathogens include *Salmonella, Escherichia Coli, Listeria*, Norwalk virus, and others. Additionally, the present technology can be used for chemical and biochemical assays. These assays can comprise mediators (chromophores, redox mediators, fluorophores) or amplification components (enzymes, electrocatalysts, etc.).

The present technology provides devices and methods for detecting or measuring (quantitatively or qualitatively) unwanted materials as analytes in a consumer product sample, using one or more analytical methods. Such devices and methods are preferably "point of use" wherein the devices are designed for use by individuals having little or no technical training, in an economically efficient manner at the point-of-sale or point-of consumption of a consumer product. Thus, for example, devices may be designed for cost-effective, reproducible and reliable detection of undesired materials. The devices may be "table top" units in a retail or home setting.

Device for Measuring Analytes

The present technology provides for a device for measuring analytes in a sample. The sample can be a consumer product. With reference to FIGS. 1A and 1B, a device 10 for measuring analytes in a sample is depicted in an open conformation (FIG. 1A), and in a closed conformation (FIG. 1B). The device comprises a housing 12, a sample chamber 14, one or more pumps (not pictured), one or more detectors (not pictured), a stirrer (not pictured), electrical contacts 16, a magnetic manipulator (not pictured) and a lid 18. The housing 12, comprises a floor 20, walls 22 and a ceiling 24 that define an interior compartment 26 and the sample chamber 14.

The sample chamber 14 is located within the housing 12. The sample chamber 14 is configured to accept the insertion of a sample cartridge 40 that comprises three chambers and electrodes (see FIGS. 2A-2D for a detailed description of the sample cartridge). The electrical contacts 16 are located within the sample chamber 14 for electronic and/or fluidic connection to the sample cartridge 40 in such a manner that the electrical contacts 16 can receive a detectable signal from the sample cartridge 40. The stirrer is functional to stir or mix contents of the sample cartridge 40 pneumatically, magnetically, acoustically or by sonication, when the sample cartridge 40 is inserted into the sample chamber 14 (see FIG. 1B for a depiction of the sample cartridge 40 inserted into the sample chamber 14).

The magnetic manipulator can be located adjacent to the sample chamber 14 and coupled to a mobile platform. In some embodiments, magnetic particles/nanoparticles can be present within the sample cartridge 40. When a sample cartridge 40 containing magnetic particles/nanoparticles is inserted into the sample chamber 14 of the device 10, the magnetic manipulator can induce a magnetic field that attracts the magnetic particles/nanoparticles and drags them to a desired location within the sample cartridge 40, i.e., to the middle compartment, by means of the mobile platform. The magnetic field can be induced with electrical power to an electromagnetic or with a permanent magnet. Non-limiting examples of permanent magnets include neodymium iron boron magnets, iron magnets, and samarium cobalt magnets. The use of a permanent magnet minimizes background noise from interferences in a sample. The magnetic particles/nanoparticles are detected preferably in a blue color spectrum.

The one or more detectors are located within the housing 12. A sample can be transferred into a sample cartridge 40, and the sample cartridge 40 can be placed into the sample chamber 14 of the device 10 (specifically depicted in FIG. 1B). The one or more detectors can detect the presence of analytes within the samples. The one or more detectors can measure pH, conductivity, current, potential, capacitance, resistance, charge, photons, temperature, viscosity, and combinations thereof. The one or more detectors can be a potentiostat, galvanostat, multimeter, electrochemical impedance analyzer, UV-Vis spectrometer, near infrared spectrometer, Fourrier transform infrared spectrometer, photomultiplier tube, photodiode, CCD, thermocouple, and combinations thereof. In some embodiments, the photomultiplier tube and/or photodiode are connected to a mobile platform, whereby the mobile platform allows for controlled movement of the photomultiplier tube and/or photodiode along the sample cartridge 40 for measurement through various locations of a sample cartridge 40. The device 10 can also comprise at least one signal processing component, such as a microcontroller or a microprocessor. Additionally, the device 10 can comprise a data storage component, such as a solid state drive with memory, software equipment, data transfer modules, and communication modules. Non-limiting examples of communication modules include Wi-Fi, Bluetooth, and ZigBee. The device 10 can also comprise a bar code reader that can read universal product code (UPC) or quick response (QR) code. Additionally, the device 10 can comprise a user interface 39 operable to display results of an analysis.

The lid 18 is functionally coupled to the housing 12 by a hinge, which enables an open conformation (FIG. 1A) and a closed conformation (FIG. 1B). In the closed conformation, light exterior to the device 10 is unable to enter the interior compartment 26, or the sample chamber 14, of the device 10.

Additionally, the lid 18 comprises seals 28, actuators 30, and injectors 32. The actuators are functional to position the seals above a sample cartridge to produce a hermetic seal on top of the sample cartridge. The injectors are positioned through the seals hermetically. In various embodiments, the injectors can inject gas, such as air, or a fluid into the sample cartridge.

Sample Cartridge

The present technology provides for a sample cartridge for a device that measures analytes. With reference to FIGS. 2A-2D, a sample cartridge 40 for a device that measures analytes is depicted in a 3-dimensionally orientation (FIG. 2A), from above (FIG. 2B), from a side face (FIG. 2C), and from a front/back face (FIG. 2D). The device 40 comprises three separate compartments, a first outer compartment 42, a second outer compartment 44, and a middle compartment 46. The first outer compartment 42 is interconnected with the middle compartment 46 by channel 48, and the second outer compartment 44 is interconnected with the middle compartment 46 by channel 50. This configuration ensures that solutions or suspensions in the outer compartments 42, 44 will not enter the middle compartment 46 via the channels 48, 50 without an increase in pressure in the outer compartments 42, 44 or a decrease in pressure in the middle compartment 46. In some embodiments, a first wall 47 separates the first outer compartment 42 and the middle compartment 46, and a second wall 49 separates the second outer compartment 44 from the middle compartment 46. In such an embodiment, the channels 48, 50 are narrow relative to the walls 47, 49, and are located proximate to a front or back face of the cartridge 40. A channel entrance can be flush with an interior wall that separates the middle compartment 46 from either of the outer compartments 42, 44 to enable smooth transfer of dragged magnetic nanoparticles between the outer compartments 42, 44, and the middle compartment 46.

The first outer compartment 42 has an opening 52, and the second outer compartment 44 has an opening 54. The openings 52, 54 allow a user to fill the outer compartments 42, 44 with solutions or suspensions. Optionally, one or both of the outer compartments 42, 44 can be prefilled with a solvent, such as water, during manufacturing of the cartridge 40. Also, the openings 52, 54 are capable of being hermetically sealed with the seals 28 (FIG. 1B) of a device 10 (FIGS. 1A and 1B) for measuring analytes in a sample.

The cartridge 40 is functional to accept a solvent and a sample. Typically, a solvent is transferred into outer compartment 42, and a sample is transferred into outer compartment 44. One or both of the outer compartments 42, 44 can comprise an integrated filter 56 for the removal of large solid particles or agglomerates that can be detrimental to analytical measurements or impair fluid and magnetic nanoparticle transfer by clogging the channels. The filter can be composed of cellulose, cotton, polymer, plastic, ceramic, metal, or combinations thereof.

The cartridge 40 further comprises integrated electrodes 58 or screen printed electrodes (not shown). When the cartridge 40 is inserted into an analytical device, such as the device 10 of FIGS. 1A and 1B, the integrated electrodes 58 or screen printed electrodes contact the electrical contacts 16 within the sample chamber 14 of the device 10 for electrochemical analyses. Furthermore, at least the front face and back faces (FIG. 2D) of the cartridge 40 are composed of an optically clear material. The optically clear material can be a clear plastic, such as polymethyl methacrylate (PMMA), or polystyrene (PS), or the optically clear material can be quartz or glass. The optically clear material allows for a detectable light beam signal to pass through the cartridge 40. In some embodiments, the cartridge is disposable.

System for Detecting Unwanted Materials

The present technology provides a system for detecting unwanted materials in a consumer product. Unwanted materials can be pesticides, insecticides, herbicides, poisons, toxicants, heavy metals, allergens, harmful pathogen microorganisms, bacteria, viruses, and combinations thereof. The system comprises a product sample cartridge comprising a product sample reservoir and a solvent reservoir and a detection port in communication with the product sample and solvent reservoirs; and a detection apparatus comprising a receptacle for the cartridge, a detection device operable to communicate with the detection port of the sample cartridge, and a user interface operable to display results of the analysis of the consumer product. The system can additionally comprise an analytical element operable to detect the unwanted material and produce a signal regarding the presence of the unwanted material. The analytical element can be contained within the product sample cartridge, the detection device, or a combination thereof. The detection device can be a potentiostat, galvanostat, multimeter, electrochemical impedance analyzer, UV-Vis spectrometer, near infrared spectrometer, Fourier transform infrared spectrometer, photomultiplier tube, photodiode, CCD, thermocouple, or combinations thereof. The one or more detectors measure pH, conductivity, current, potential, capacitance, resistance, charge, photons, temperature, viscosity, or combinations thereof. The signal can be mechanical, electrical or optical. The system can be suitable in size to be used on a table top or counter top.

Method for Measuring Analytes

The present technology also provides for a method for measuring analytes in a consumer product with or without a chemical or biochemical assays. Food and beverage safety and quality are a constant issue. Therefore, testing for the presence of pesticides, insecticides, herbicides, harmful pathogen microorganisms, bacteria, and viruses on fruits and vegetables is desirable. Additionally, consumers are interested in water quality, detection of metal and/or microbial contaminants in water, the determination of whether a food product contains an allergen, and testing of whether a food product is caffeine-free, peanut-free, shellfish-free, gluten-free, and/or lactose-free. Furthermore, the present technology can be used to detect drugs and other chemicals or biomarkers in human or animal urine, or other biological fluid. Also, the present technology can be applied to test the quality of aquarium water, to analyze household contaminants, such as mold, or to perform air quality measurements. A non-limiting list of uses for the present technology includes: food analysis, including the presence of pesticides and surface cleanness; determination of the presence of harmful bacteria in food; food safety; determination of the amount of sugars in food; the identification of sugars in food; determination of the presence and concentration of caffeine; determination of the presence and concentration of gluten; the determination of the presence and concentration of lactose; determination of the presence of nuts; milk quality; determination of the presence and concentration of mercury; determination of the quality of dairy products, including living cultures in yogurts; determination of the safety and quality of perishable stored foods; determination of the presence of toxins; drug tests; water quality; aquarium tank water quality; mold analysis of structures, air conditioner filters, etc.; determination of the presence and concentration of monosodium glutamate (MSG); air quality, including the presence and concentration of pollutants; and the determination of the presence and concentration of alcohol in liquids, including beverages.

The cartridge operation and device performance of the present technology is based on contactless, cross-contamination free, digitally controlled automatic sample processing, and analyte detection in the cartridge. The sample can be prepared from a consumer product, or it can be an element of a chemical or biochemical assay. The method for measuring analytes in a sample comprises obtaining a sample cartridge comprising a first outer compartment, a second outer compartment, a middle compartment, and integrated electrode pairs and/or screen printed electrodes, wherein the first outer compartment and the second outer compartment are interconnected to the middle compartment by channels; obtaining a measuring device comprising a sample chamber, one or more pumps, one or more detectors, a stirrer, electrical contacts, a magnetic manipulator and a closable lid, wherein the closable lid comprises seals, actuators and injectors; transferring a solvent into the first outer (solvent) compartment of the sample cartridge; preparing a sample in a sample solvent; transferring the sample into the second outer (sample) compartment of the sample cartridge; inserting the sample cartridge into the sample chamber of the measuring device; closing the lid; automatic sample processing; and detecting the presence of an analyte. The sample can comprise a suspension. In some embodiments, a filter is integrated into at least one of the outer compartments of the sample cartridge allowing for filtering of the solvent or sample after being transferred into the sample cartridge. When the lid is closed, the actuators position the seals to produce a hermetic seal on the outer compartments of the sample cartridge. The injectors can then be operated to induce pneumatic pressure into the outside chambers, thereby transferring the sample and the solvent from the outer compartments, through the channels, and into the middle compartment. The current technology contemplates transferring rates of from about 20 µL/s to about 1000 µL/s. Preferably, the transferring rate is from about 100 µL/s to about 200 µL/s. Preferably, the transferring rate is about 180 µL/s. The current method allows for contactless and cross-contamination free transferring of sample and solvent from within the sample cartridge and automatic sample preparation in the middle (detection) compartment. In some embodiments, the contents of the middle compartments are stirred or mixed pneumatically, magnetically, acoustically, or by sonication.

In some embodiments, magnetic nanoparticles can be transferred into the sample or are pre-inserted in the first outer compartment of the sample cartridge. A non-limiting example of a magnetic nanoparticle is gold coated iron oxide ($Fe_3O_4$) nanoparticles. The magnetic nanoparticles can be modified with a detection active material. Antibodies, aptamers, enzymes, and molecularly imprinted polymers are non-limiting examples of detection active materials. In some embodiments, the antibodies can comprise a label or a tag that is capable of producing a detectable signal. The magnetic nanoparticles can then be transferred into the middle compartment by the magnetic manipulator. Therefore, the magnetic nanoparticles modified with a detection active material can be used to carry/drag an analyte from the first outer sample compartment of the sample cartridge to the middle compartment. The magnetic manipulator can be coupled to a mobile platform. The magnetic manipulator can induce a magnetic field capable of dragging the magnetic nanoparticles from the second outer (sample) compartment of the sample cartridge to the middle compartment. The magnetic field can be induced with electrical power to an electromagnet or with a permanent magnet. Non-limiting examples of permanent magnets include neodymium iron boron magnets, iron magnets, and samarium cobalt magnets. The use of a permanent magnet minimizes background noise from interferences in a sample. In some embodiments, the magnetic nanoparticles are detected preferably in a blue color spectrum.

According to the method, detecting is performed by a potentiostat, galvanostat, multimeter, electrochemical impedance analyzer, UV-Vis spectrometer, near infrared spectrometer, Fourier transform infrared spectrometer, photomultiplier tube, photodiode, CCD, thermocouple, or combinations thereof. The one or more detectors measure pH, conductivity, current, potential, capacitance, resistance, charge, photons, temperature, viscosity, or combinations thereof. For example, when the sample cartridge is inserted into the sample chamber of the device, the electrode pairs in a two or three electrode setup can be measured at a given voltage. Alternatively, voltage can be measured for a given constant current, or another electrochemical method can be applied, including: coulometry, amperometry, cyclic voltammetry, linear scan voltammetry, differential pulse voltammetry, differential pulse amperometry, pulsed amperometric detection, square wave voltammetry and/or electrochemical impedance spectroscopy. The device can further comprise a user interface operable to display results. Depending on the results, additional measurements with higher or lower sample concentration may be required. Sample concentration in the middle compartment of the cartridge can be adjusted by pneumatically transferring more sample from the second outer (sample) compartment to the middle compartment, and/or by transferring less solvent from the first outer (solvent) compartment to the middle compartment

EXAMPLES

The following specific examples are provided for illustrative purposes of how to use the device, cartridge and method of this technology.

I. Solutions are Transferred from the Outer Compartments of a Sample Cartridge to the Middle Compartment by a Pneumatic Filling System.

Pure water (representing a solvent) was transferred into a first outer (solvent) compartment of a sample cartridge. Water containing blue dye (representing a sample solution) was transferred into a second outer (sample) compartment of the sample cartridge. The outer compartments were hermetically sealed with seals and an injector was inserted through each seal without disrupting the hermetic seal. The insertion of the injectors did not compromise the hermetic seal. The injectors were connected to pump, which supplied pneumatic pressure. The following steps were then performed:

1. transfer 920 µL of the water containing dye from the second outer (sample) compartment to the middle compartment at a flow rate of 180 µL/s; and
2. transfer 850 µL of water from the first outer (solvent) compartment to the middle compartment at a flow rate of 180 µL/s.

A video of the process was recorded and still photographs of the filling time progression from the video are shown in FIG. 3. When looking at FIG. 3, the left compartment contains the pure water and the right compartment contains the water with dye. Frame A is a photograph of the cartridge at t=0, where "t" represents time. Frame B shows the system at t=1 s, and frame C shows the system at t=5 s. After 5 seconds, 900 µL of the water containing dye was transferred to the middle compartment, and no pure water had been transferred. Frames D, E, and F show the system at t=6 s, t=9 s, and t=11 s respectively, wherein the pure water is pumped into the middle chamber. The sample cartridge and the pneumatic filling system allows filling of the middle compartment with solutions from the outer compartments in any order, including simultaneously. Also, the system allows a wide range of flow rates including time variable (dynamic) transfer, and controlled volume of transferred liquid independently for sample and solvent.

II. A Test is Performed to Determine Whether Lettuce Labeled "Organic" in the Supermarket Contains Pesticide.

First, a sample is processed. A leaf of lettuce is cut into small pieces. The small pieces of lettuce and a volume of sample solvent are placed within a handheld homogenizer. The lettuce is then homogenized with the use of a pestle. The resulting solution is the "sample."

Next, a volume of the sample solvent is transferred to a first outer (solvent) compartment of a sample cartridge via a first opening. A volume of the sample is then transferred above a filter integrated in a second outer (sample) compartment of the sample cartridge, via a second opening, and into the second outer compartment. The sample cartridge further comprises a third compartment, located in between the two outer compartments, and integrated electrodes. The two outer compartments are connected to the middle compartment by channels.

The sample cartridge is next inserted into the sample chamber of a device for measuring analytes. The integrated electrodes of the sample cartridge contact electronic contacts within the sample chamber.

The analytical device comprises a lid comprising seals, and actuators. When the lid is closed, the actuators are operated to move the seals into first and second openings to form a hermetic seal. Alternatively, the hermetic seal is established mechanically when the lid is closed manually by a user. Injectors are integrated with the seals. A pump within the device is then operated to increase the pressure within the first outer (solvent) compartment by injecting gas through an injector into the first outer compartment. The sample solvent within the first outer compartment is thereby pneumatically transferred into the middle compartment. The device can then apply a constant voltage by means of the electrical contacts, and measure a background current from the sample solvent.

Next, a second pump within the device is operated to increase the pressure within the second outer (sample) compartment by injecting gas through an injector into the second outer compartment. The sample within the second outer compartment is thereby pneumatically transferred into the middle compartment, to form a diluted sample. The diluted sample is then mixed pneumatically by providing repetitive short pulses of gas in alternating directions. The device again applies a constant voltage, and measures a current through the diluted sample. The device compares the current obtained from the diluted sample with the background current to determine whether pesticide is present in the sample. Results of the test are displayed on a user interface.

Non-Limiting Discussion of Terminology

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Individual elements or features of a particular embodiment are generally not limited to that particular embodiment, but, where applicable, are interchangeable and can be used in a selected embodiment, even if not specifically shown or described. The same may also be varied in many ways. Specific examples are provided for illustrative purposes of how to make and use the compositions and methods of this technology and, unless explicitly stated otherwise, are not intended to be a representation that given embodiments of this technology have, or have not, been made or tested. Equivalent changes, modifications and variations of some embodiments, materials, compositions and methods can be made within the scope of the present technology, with substantially similar results.

As used herein, the words "prefer" or "preferable" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components or process steps, the present technology also specifically includes embodiments consisting of, or consisting essentially of, such materials, components or processes excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein. Further, as used herein the term "consisting essentially of" recited materials or components envisions embodiments "consisting of" the recited materials or components.

When an element or layer is referred to as being "on," "connected to," or "coupled to" another element or layer, it may be directly on, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

"A" and "an" as used herein indicate "at least one" of the item is present; a plurality of such items may be present, when possible. "About" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters.

As referred to herein, ranges are, unless specified otherwise, inclusive of endpoints and include disclosure of all distinct values and further divided ranges within the entire range. Thus, for example, a range of "from A to B" or "from about A to about B" is inclusive of A and of B. Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

What is claimed is:

1. A system for detecting unwanted materials in a consumer product, comprising:
    (a) a product sample cartridge comprising a first outer compartment configured to receive a solvent, a second outer compartment configured to receive a sample of the consumer product, a middle compartment positioned between the first and second outer compartments configured to receive at least a portion of the solvent from the first outer compartment and at least a portion of the sample from the second outer compartment, an optically clear front face, an optically clear back face, and electrodes positioned in the middle compartment, wherein the first outer compartment and the second outer compartment are interconnected to, and in communication with, the middle compartment by channels, and wherein transfer of the solvent and the sample contained in the outer compartments to the middle compartment is performed by increasing pneumatic pressure individually in the corresponding outer compartments or decreasing pneumatic pressure in the middle compartment; and
    (b) a detection apparatus comprising a receptacle for the cartridge, a closable lid comprising injectors that communicate with the outer compartments of the sample cartridge when the lid is closed, the injectors being operable to provide the increasing or decreasing pneumatic pressure, a detection device comprising one or more detectors operable to communicate with the optically clear front face, optically clear back face, and/or electrodes of the sample cartridge, and a user interface operable to display results of the analysis of the consumer product,
    wherein the system is configured to detect specific unwanted materials in the consumer product.

2. The system according to claim 1, additionally comprising a detection active material operable to detect the unwanted material and produce a mechanical, thermal, electrical, or optical signal regarding the presence of the specific unwanted material.

3. The system according to claim 2, wherein the detection active material is an antibody, aptamer, enzyme, or a molecularly imprinted polymer, which is contained within the product sample cartridge.

4. The system according to claim 1, wherein the detection device comprises a housing, a sample chamber, one or more pumps, a stirrer, electrical contacts, and a magnetic manipulator.

5. The system according to claim 4, wherein the sample cartridge is inserted into the sample chamber.

6. The system according to claim 4, wherein the one or more detectors measure pH, conductivity, current, potential, capacitance, resistance, charge, photons, temperature, viscosity, or combinations thereof.

7. The system according to claim 4, wherein the one or more detector is a potentiostat, galvanostat, multimeter, electrochemical impedance analyzer, ultraviolet-visible (UV-Vis) spectrometer, near infrared spectrometer, Fourrier transform infrared spectrometer, photomultiplier tube, photodiode, charge-coupled device (CCD), thermocouple, or combinations thereof.

8. The system according to claim 7, wherein the photomultiplier tube and/or photodiode are connected to a mobile platform, whereby the mobile platform allows for controlled movement of the photomultiplier tube and/or photodiode for measurement through various points in a sample cartridge.

9. The system according to claim 4, wherein the lid further comprises seals and actuators, wherein the actuators are functional to move the seals to produce a hermetic seal at an opening of a sample cartridge when a sample cartridge is inserted into the sample chamber and the lid is in a closed conformation.

10. The system according to claim 1, further comprising data transfer and communication modules.

* * * * *